United States Patent [19]

Firth

[11] Patent Number: 5,252,822
[45] Date of Patent: Oct. 12, 1993

[54] CONTACT WHEEL AUTOMATED DIGITIZER WITH VISIBLE SENSING OF MARKED REFERENCE POINTS

[75] Inventor: David G. Firth, Seattle, Wash.
[73] Assignee: Pruvel Corporation, Seattle, Wash.
[21] Appl. No.: 951,907
[22] Filed: Sep. 28, 1992
[51] Int. Cl.⁵ .................................................. H01J 5/16
[52] U.S. Cl. .................... 250/227.11; 250/560
[58] Field of Search ............... 250/227.11, 231.10, 250/560; 33/503, 505

[56] References Cited

U.S. PATENT DOCUMENTS 3,812,376  5/1974  Takeyama et al. ............. 250/227.11

Primary Examiner—David C. Nelms
Attorney, Agent, or Firm—Connolly & Hutz

[57] ABSTRACT

A digitizer for use in computer aided design and manufacturing (CAD/CAM) systems for making orthotic and prosthetic devices includes a movably mounted pendent arm having a free end with a contact wheel mounted to the free end for making rolling contact with the surface of a three dimensional shape to create reference points for the CAD/CAM to accurately create an orthotic or prosthetic device. The digitizer is automated by mounting a sensor tip at the free end of the pendent arm for automatically visibly sensing marked reference points on the surface of the shape.

8 Claims, 2 Drawing Sheets

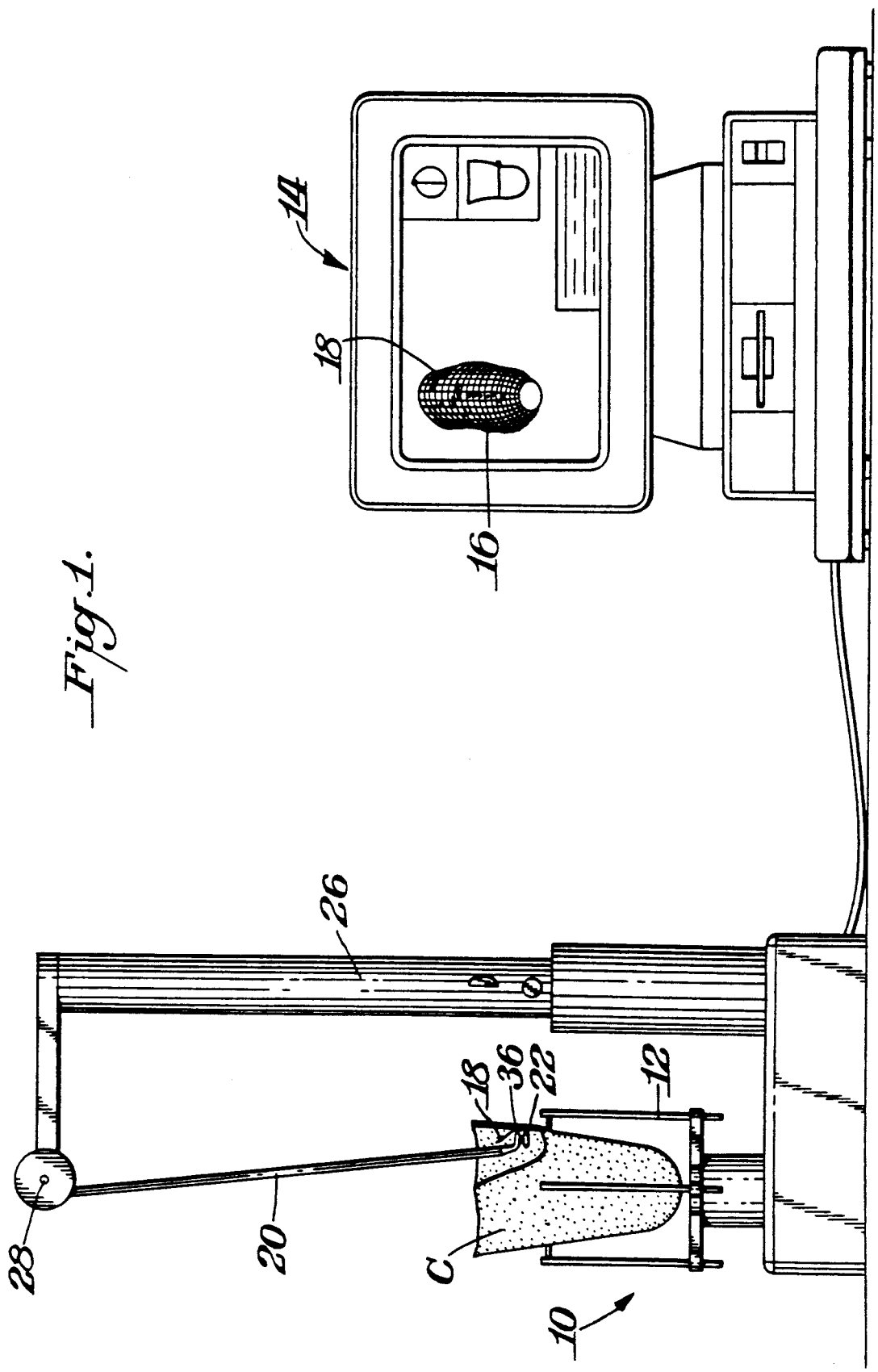

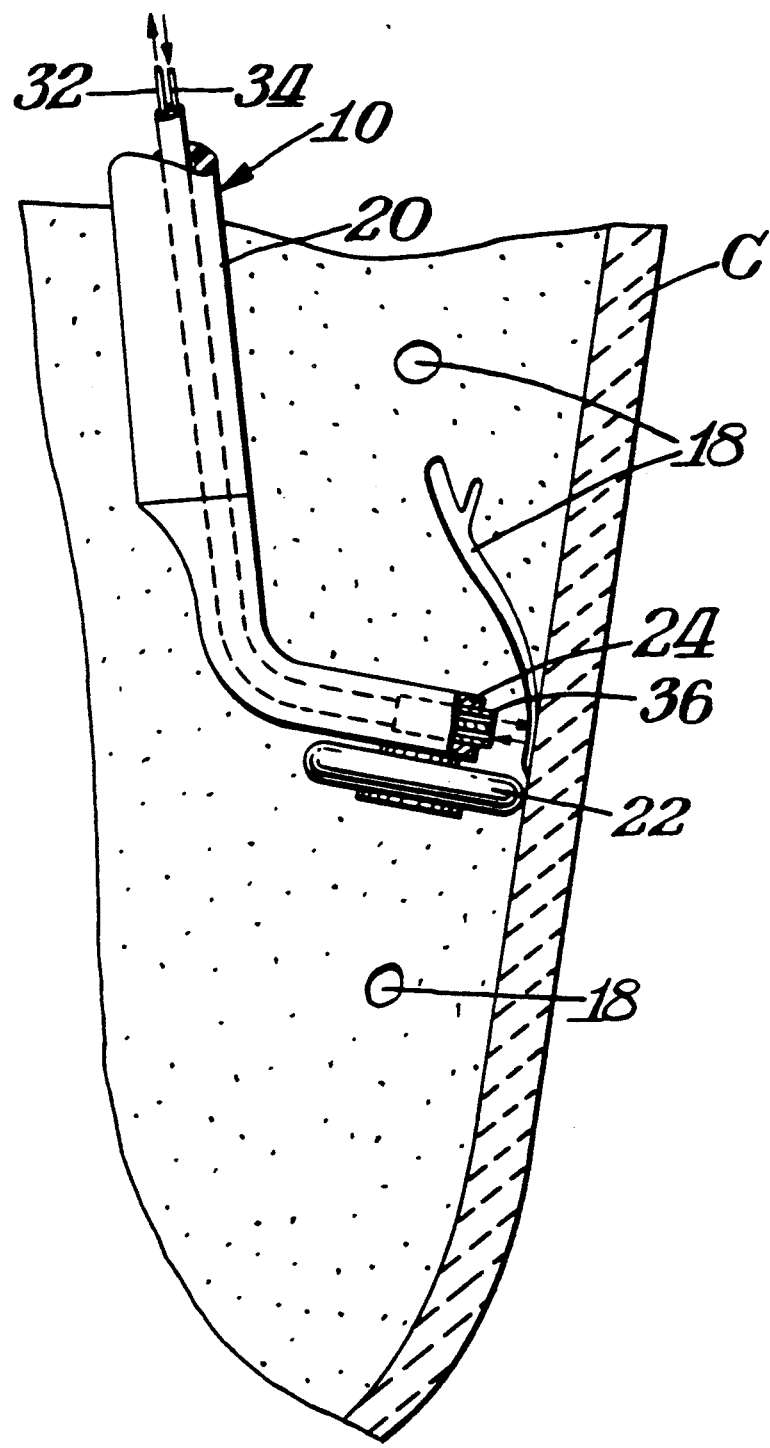

CONTACT WHEEL AUTOMATED DIGITIZER WITH VISIBLE SENSING OF MARKED REFERENCE POINTS

BACKGROUND OF THE INVENTION

Digitizers are utilized in the art in the manufacture of orthotic and prosthetic devices such as artificial limbs and braces. Such digitizers are used for sending positional reference points of a three dimensional shape to the computer aided design and manufacturing (CAD/CAM) systems. In such practice the shape of the residual limb of the amputee, for example, is converted into a series of data points from which a computer can construct a three dimensional model of the residual limb. Digitizers are the instruments used to perform this shaped measurement function. In practice the prosthetist uses a marking pen to draw or mark certain important anatomical features on the residual limb which are later used when designing the proper socket shape. These marks indicate areas of irregularity, such as scar tissue or standard anatomical features as other reference points on the residual limb. A plaster cast would be made around the residual limb with the cast being the reverse or female model of the residual limb and with the marks denoting the important reference points. The marks are transferred to the inner surface of the plaster cast. A known digitizer includes a movable pendent arm having a contact wheel at its free end for making rolling contact with the inner surface of the cast. Prior contact wheel digitizers require constant attendance by a prosthetist to assure the proper capturing of the visibly marked positional reference points.

Traditional, labor intensive techniques for designing and fabricating an artificial limb typically require between 15-40 hours of direct labor input by a prosthetist and a fabrication technician. The largest portion of this time (upwards of 50%) is spent creating the socket portion of the limb—the precisely shaped hollow area in the prosthetic limb into which the amputee places his or her residual limb (stump).

SUMMARY OF THE INVENTION

An object of this invention is to provide an automated contact wheel digitizer which avoids the need for manual attendance in operating the digitizer and thus avoids the labor intensive techniques which plague the prior art.

A further object of this invention is to provide a method of digitizing which can be automatically accomplished without the constant need for manual attendance.

In accordance with this invention, the digitizer makes use of the known contact wheel digitizer techniques by including a movably mounted pendent arm having a free end with a contact wheel mounted to the free end for making rolling contact with the surface of a three dimensional shape for creating reference points for the CAD/CAM. The invention, however, includes a sensor tip mounted to the free end of the pendent arm for automatically visibly sensing the marked reference points without requiring manual attendance for noting these marked reference points.

In the preferred practice of this invention the sensor tip is of non-contact construction utilizing fiber optics.

The digitizer of this invention provides a CAD/CAM approach to artificial limb and brace fabrication which enables prosthetists and orthotists to provide a large quantity of better quality artificial limbs and braces at lower costs to patients and/or third party insurance carriers by substantially reducing the time of labor input. Thus, with the practice of the invention the most significant labor input would be the few hours required during which a prosthetist can often complete this socket design and fabric process.

THE DRAWINGS

FIG. 1 is a front elevational view schematically illustrating a digitizer in accordance with this invention as used with a cast and showing the cast partly cut away; and FIG. 2 is a cross-sectional view on an enlarged scale of the digitizer shown in FIG. 1.

DETAILED DESCRIPTION

Before discussing the specific features of the invention the following description points out the general practices used by the prior art and which are also utilized with the invention.

The first step in the CAD/CAM approach to limb making is converting the shape of the amputee's residual limb into a series of data points from which a computer can construct a three dimensional model of the residual limb. The present invention is concerned with the use of a contact wheel digitizer to perform this shape measurement function.

An artificial limb consists of the following general components:

Socket—the precisely shaped, concave area into which the residual limb fits. Proper fit of the socket is the most critical aspect of an artificial limb. Because of this, the socket is almost always fabricated first and as a separate component, test fit on the amputee, and only after a satisfactory fit is achieved, then incorporated into an overall artificial limb. Every socket must be custom designed specifically to fit the individual residual limb of each amputee.

It is important to note that the proper shape of the socket is not simply a duplicate of the shape of the residual limb itself. The socket must be shaped so that it fits very tightly in areas where the residual limb can support the full weight of the body. It must be loose in areas where the residual limb is sensitive. The final shape of a well fitting, highly functional socket is often surprisingly different than that of the residual limb, much as a shoe is not an exact reverse of the shape of a foot. Making the judgements necessary to create a proper, functional shape for the socket is one of the key professional skills of the prosthetists.

Foot—Most lower limb prostheses will use one of many standard available foot components.

Shank—The socket will be connected to the foot with a section of tubing called the shank.

Cosmetic Cover—A cosmetic cover will be formed over the socket and shank and smoothed to meet the shape of the foot.

There are many variations of foot, shank, and cosmetic cover. However, every limb must contain a socket which has been custom designed, fit, and fabricated for each amputee.

The traditional limb making techniques utilize reference points in limb design and fabrication process. The present invention involves automatically sensing these reference points when using a CAD/CAM design and fabrication process.

In designing and fabricating the socket, the prosthetist first pulls a thin elastic sheath of fabric over the amputee's residual limb. The prosthetist will use a marking pen to draw and/or mark certain important anatomical features on the residual limb for later use when designing the proper socket shape. These marks could indicate areas of scar tissue, standard anatomical features such as the patellar tendon (tendon under the knee cap) or crest of the tibia (shin), or other reference points on the residual limb. These marks will typically be made on the fabric sheath with an indelible marking pencil.

Once the prosthetist has marked the appropriate reference points, the prosthetist will wrap casting plaster around the residual limb of the amputee. After this plaster hardens, the prosthetist will pull the cast from the residual limb. The resulting cast is a reverse (female) model of the residual limb, with marks denoting important reference points. The marks transfer from the thin fabric sheath placed on the residual limb to inside surface of the plaster cast, as the sheath itself becomes the inside surface of the cast.

The prosthetist then fills this female plaster cast model with liquid plaster. This liquid plaster hardens and is then removed from the female cast model. The result is a plaster duplicate (male model or positive shape) of the amputee's residual limb. This plaster positive model will also show the prosthetist's marks on the reference points.

In traditional limb making techniques, the prosthetist creates the physical shape of the socket by either carving plaster away or adding more plaster to the positive plaster model of the residual limb. During this process the prosthetist will make extensive use of the marked reference points as the prosthetist designs the shapes, positions, and magnitudes of the modifications to the shape of the model of the residual limb.

When the positive plaster model has been hand modified into an appropriate socket shape, the prosthetist will use any number of fabrication techniques such as vacuum forming or fiberglass lamination to form the actual socket shape over this model.

After test fitting the initial socket design on the amputee and likely one or two more rounds of socket shape modification, a final socket will then be incorporated in other final artificial limb using a variety of fabrication techniques and other components (foot section, cosmetic cover, etc).

The CAD/CAM approach does not radically change the general steps described above, nor is it used for all phases of limb fabrication. It does, however, create efficiency and precision in much of the most labor intensive and skill dependent part of the process-the duplication of the shape of the residual limb, modification of this shape into an appropriate socket shape, and creation of a three-dimensional plaster model over which the final socket can be formed.

As with traditional techniques, the prosthetist starts by marking important anatomical reference points on the residual limb and making a plaster cast of its shape.

As shown in the drawing the prosthetist then places the cast C in a digitizer 10 to measure the shape of the cast and convert those measurements into data coordinates. The digitizer 10 must also provide a method for specifically distinguishing the marked reference points from the basic shape points.

This shape and reference point data is transferred to a computer 14 running a CAD/CAM software program specifically written for use in artificial limb and brace making. The CAD/CAM software uses the data from the digitizer 10 to create a three dimensional model 16 of the shape of the residual limb on the computer screen. Reference points 18 will be highlighted in this model 16. This step is analogous to the prosthetist using traditional techniques to create the three dimensional plaster positive model by pouring liquid plaster into the cast from the amputee. The prosthetist has created a duplicate model of the residual limb (albeit a computer model); the prosthetist must now design the socket appropriate for that shape.

The prosthetist will now use the CAD/CAM software to design the socket. The prosthetist will use the software to simulate removing and adding material from the computer model of the residual limb, much as would have been physically done by hand on the plaster model. As with the traditional process the majority of the prosthetist's critical design decisions are based on the position and shape of the marked reference points. These reference points 18 will be highlighted in some way on the computer view of the residual limb shape. The software offers many levels of control and automation which significantly decrease the time it takes to complete this design process. In addition, it provides a detailed record of the starting shape of the limb and the magnitude and shape of the modifications made by the prosthetist. In many cases, it can take a prosthetist 10-20 minutes to complete the CAD/CAM design of a socket which would have taken hours using traditional techniques.

When the prosthetist has completed the design of the socket, the socket fabrication phase is begun. The CAD/CAM software is used to control a specialized lathe. This lathe will carve a cylindrical blank of solid plaster into a positive model of the socket shape he designed on the computer. At this point the prosthetist may again use a variety of techniques to form a test socket. Any further modifications to the design can be quickly made on the computer, and a new positive model carved using the lathe. When satisfied with the socket design, the prosthetist can use all standard techniques and components to fabricate the final limb, using the carved plaster positive model to form the socket.

The steps described in both the traditional and CAD/CAM approach to design and fabrication of a lower limb prosthesis are also used for fabrication of many other orthotic and prosthetic devices, from custom fit knee braces and artificial arms, to spinal body jackets. The prosthetist will make a plaster model of the patient, modify this shape, and uses the modified model as the forming tool for fabrication of the custom fit brace of limb. Reference points will also be used in fabricating these devices. The CAD/CAM approach is not limited to design and fabrication of lower limbs for amputees—it can be successfully used in all phases of orthotic and prosthetic work.

The illustrated digitizer 10 fits in a class of instruments known as contact wheel digitizers. Variations of these for use in orthotic and prosthetic CAD/CAM systems have been commercially available for the past three or so years. Similarities between all contact wheel digitizers include a vertical probe or pendent arm 20 which extends into the cast shape or adjacent the positive model shape with a horizontal wheel 22 on the offset free end 24 of this arm 20. This entire probe arm/contact wheel assembly can travel vertically on a slide mechanism 26. The probe arm/contact wheel mechanism also swings from an axis 28 at the top.

Prior art contact wheel digitizers of this type include the Digitshape by Shape Products Limited, (SPL) and a product by Applied Biotechnology Limited, (ABT). These devices are described in the brochures "The Future's In Great Shape" and "DigitShape". The Seattle Digitizer by Model and Instrument Development also uses this format which is contemporaneous with this invention and described in the brochure "Seattle Digitizer TM Specifications". Since the present invention utilizes some of these basic features, the details of these three brochures are incorporated herein by reference thereto. There have been demonstrations of other forms of devices to digitize the shape of an amputee's residual limb. The majority of these are based on some form of direct laser/video scanning on the residual limb itself, and are thus referred to as non-contact digitizers, as there is no contact between the digitizer and the surface being digitized.

The prior art contact wheel digitizers are used for measuring the shape. The cast or model to be digitized is placed in a chuck or holder 12 which rotates the cast C or model during the digitizing cycle. The probe arm/contact wheel is then moved to the bottom of the cast or model, with the contact wheel 22 resting against either the inside surface of a cast or the outside of a positive model.

The digitizing sequence is then initiated. The cast or model rotates while the probe arm/contact wheel follows the contour of the shape. The entire probe arm/contact wheel assembly also travels continuously upward a fixed amount (usually ¼ to 1/5 of an inch) during each rotation of the cast. Thus, the probe arm/contact wheel traces a continuous spiral from the bottom to the top of the cast or positive model.

Throughout this spiral tracing step, the horizontal position of the probe arm 20 is measured by a radial encoder. The rotational position of the cast is measured by a second encoder. The vertical position for the probe arm/contact wheel can either be measured by a third encoder or calculated because it travels in a fixed relationship to the rotation of the cast in the chuck 12. These measurements then allow the shape of the cast C to be described as a series of positional data points. The physical shape of the cast or model has thus been converted into a series of data describing three dimensional points in space.

The digitizer 10 of this invention uses this general process for measuring the shape of either a female cast or for male positive model shape.

The prior art contact wheel digitizers are used for capturing reference points. As with the traditional process, duplicating the shape of the residual limb is not enough. The prosthetist requires specific reference points to be highlighted in the shape.

All contact wheel digitizers, other than the digitizer 10 of this invention, use the following basic process for marking the reference points. In a separate step of one overall digitizing cycle, the prosthetist will use controls on the digitizer to move the probe arm/contact wheel so that the contact wheel is directly over the visibly marked reference points on the cast or model. With rotation of the cast and vertical travel of the probe arm stopped, the prosthetist will then depress either a control button on the digitizer or a key on the computer keyboard to denote that this specific position is a reference point to highlight. This process of positioning the contact wheel precisely over visible marks and pressing a key to signify this position as a reference point must be repeated for every individual reference point the prosthetist wishes to mark in the digitized shape. In some digitizers this reference marking process is completed before capturing the overall shape, in others it is completed after capturing the shape.

This separate step of positioning the probe and manually denoting each individual reference point takes time and relies upon the judgement of the operator that they have indeed positioned the probe directly over the reference point.

The digitizer 10 dramatically departs from the prior art techniques. With digitizer 10 it is possible to automate the capture of marked reference points in a contact wheel digitizer.

The primary disadvantage of the prior art techniques of manually positioning the probe and denoting reference points was that such techniques are both time consuming and prone to operator induced inaccuracy. To increase the ease and accuracy of capturing the marking reference points as well as the overall speed of the digitizing process, the digitizer 10 of this invention enables the position of reference points to be captured simultaneously with, and automatically as part of, the process of tracing the spiral to measure the basic shape of the cast.

The key departure of the invention from the prior art is the addition of a sensor tip 36 to the tip of the pendent arm 20 near the contact wheel 22. This sensor 36 would sense when the probe arm/contact wheel traveled over a visibly marked reference point 18 made in the cast by the prosthetist and would automatically denote this position as a reference point to be highlighted in the computer three dimensional model of the shape. This would occur during and without interrupting the process of measuring the basic shape of the cast or positive model and without reliance on manual positioning of the probe or keyboard entry by the prosthetist.

A particularly suitable sensor tip 36 is available from the Keyence Corp. of America, more particularly, the Keyence sensor model number FS2-60 photoelectric sensor amplifier unit and the FU-4F fiber optic unit. The tip of the fiber optic unit is mounted at the offset free end 24 of arm 20. The particular format of this sensor 36 is a small monitoring/processing unit from which emanate two separate strands of fiber optic cable 32, 34 which terminate in a small metal encased sensor tip. The processing unit sends a fixed, known amount of light out through one of the fiber optic strands 34. This light reflects off the surface being monitored and travels back into the processing unit through the second fiber optic strand 32. As the sensor tip 36 passes over an area of color change (for example passing over a black or blue reference mark 18 typically made by a prosthetist in a white plaster cast) the amount of light reflected changes. The processing unit monitors this change in reflected light and sends a signal that a "point of interest" has been sensed when the change exceeds a threshold set by the user.

Although the drawings illustrate digitizer 10 being used with the inner surface of a cast, digitizer 10 can also be used with positive shapes. The chuck 12 would be replaced with an external adapter. A pendent offset adapter would provide additional clearance for the movement around the outer surface of the external or positive shape.

The digitizer 10 of this invention wherein there is automated reference point sensing in a contact wheel digitizer has proven to have significant advantages over the prior art method of marking reference points. A summary of these advantages is the following:

Faster cycle time to complete overall digitizing process. Automated reference mark sensing provides a digitizer 10 that completes both phases of digitizing, shape capture and reference point marking, in one continuous step, reducing the time to complete one digitizing cycle by 25% to 50%.

More accurate positional placement of reference marks. Automated sensing provides a potentially more accurate method for capturing the position of reference points than the prior art, which relies on manual positioning of the probe arm. It can be difficult to visually judge whether the probe arm is truly centered over a visible mark at the bottom end of a narrow cast. Automated reference mark sensing with digitizer 10 assures that the reference point in the CAD/CAM representation of the residual limb is in the same position where it was first drawn on the actual residual limb by the prosthetist.

Ease of capturing many reference points creates new clinical opportunities. The time and trouble associated with manual capturing individual reference points using the prior art led most prosthetists to mark only a small number of single reference points—usually between 2 and 10. Automated sensing with digitizer 10 removes this disincentive, thus allowing the prosthetist to mark as many reference points as desired in the cast without increasing the burden when subsequently digitizing the cast.

This also allows the prosthetist to not only capture single marked reference points on the cast, but also more complex reference shapes such as lines and circles. These will be captured by the automated mark sensor as series of closely spaced reference points. Thus, an area of scar tissue on the residual limb could be circled on the residual by the prosthetist. The visible circle drawn in the cast would be sensed by digitizer 10 with its automated mark sensor 36 and then appear in the CAD/CAM model as a series of points in the shape of the circle. While not impossible using the prior art for reference point marking, the time and effort required to manually position the pendent over the 10 to 30 individual points necessary to define a shape such as a circle make it very impractical.

Ease of overall digitizing process. Automated reference mark sensing thus provides a digitizer which, in general, requires far less manually control by the operator, and therefore is significantly easier and more efficient to use.

I claim:

1. In a contact wheel digitizer for use in computer aided design and manufacturing (CAD/CAM) systems for making orthotic and/or prosthetic devices wherein the digitizer includes a movably mounted pendent arm having a free end with a contact wheel mounted to the free end for making rolling contact with the surface of a three dimensional shape for creating reference points for the CAD/CAM to accurately create an orthotic or prosthetic device, the improvement being in that a sensor tip is mounted to said free end of said pendent arm for automatically visibly sensing marked reference points on the surface of the shape.

2. The digitizer of claim 1 wherein said sensor tip operates as a non-contact sensor.

3. The digitizer of claim 2 wherein said sensor tip includes fiber optics strands.

4. The digitizer of claim 3 wherein said free end of said arm is offset from the remainder of said arm, said contact wheel being mounted to said offset, and said contact wheel extending outwardly beyond said sensor tip.

5. The digitizer of claim 4 wherein said fiber optics strands includes a first strand for directing light toward the surface and a second strand for directing the reflected light away from the surface.

6. In a method of making orthotic and/or prosthetic devices with the use of a contact wheel digitizer which detects reference points for CAD/CAM systems, the improvement being in automatically visibly sensing marked reference points.

7. The method of claim 6 wherein the automatic sensing is done by a non-contact sensor tip mounted to the pendent arm of the digitizer adjacent the contact wheel of the digitizer.

8. The method of claim 7 wherein the sensing includes using a first fiber optic strand which directs light toward the surface being sensed, and using a second fiber optic strand directing the reflected light away from the surface.

* * * * *